(12) United States Patent
Neumann

(10) Patent No.: US 11,211,159 B1
(45) Date of Patent: Dec. 28, 2021

(54) SYSTEM AND METHOD FOR GENERATING AN OTOLARYNGOLOGICAL DISEASE NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/136,179

(22) Filed: Dec. 29, 2020

(51) Int. Cl.
G16H 20/60 (2018.01)
G06N 20/00 (2019.01)
G16H 50/20 (2018.01)

(52) U.S. Cl.
CPC ............. G16H 20/60 (2018.01); G06N 20/00 (2019.01); G16H 50/20 (2018.01)

(58) Field of Classification Search
CPC ......... G16H 20/60; G16H 50/20; G06N 20/00
USPC .......................................................... 705/2
See application file for complete search history.

(56) References Cited

U.S. PATENT DOCUMENTS

| | | | |
|---|---|---|---|
| 2007/0071643 | A1 | 3/2007 | Hall |
| 2007/0224619 | A1 | 9/2007 | Banet |
| 2009/0299645 | A1 | 12/2009 | Colby |
| 2011/0150776 | A1 | 6/2011 | Shea |
| 2016/0246947 | A1 | 8/2016 | Yao |
| 2016/0270863 | A1* | 9/2016 | Makower .............. A61M 29/02 |
| 2017/0042463 | A1* | 2/2017 | Rajkumar .............. A61B 5/165 |
| 2017/0109499 | A1* | 4/2017 | Doshi ...................... G06F 19/00 |
| 2019/0232063 | A1* | 8/2019 | Fuerst ................. A61N 1/36014 |

(Continued)

FOREIGN PATENT DOCUMENTS

RU    2562537 C2    9/2015

OTHER PUBLICATIONS

Title: Dietary Treatment of Chronic Sinusitis Date: Dec. 1938 By: Shurly pp. 174-177.

(Continued)

Primary Examiner — Michael Tomaszewski
Assistant Examiner — Rachael Sojin Stone
(74) Attorney, Agent, or Firm — Caldwell Intellectual Property Law, LLC

(57) ABSTRACT

A system and method for generating an otolaryngological disease nourishment program comprises a computing device configured to receive at least an otolaryngological component as a function of an otolaryngological system, determine an otolaryngological localizer as a function of the otolaryngological biomarker, wherein determining comprises obtaining at least an otolaryngological assemblage, and determining the otolaryngological localizer as a function of the otolaryngological biomarker and otolaryngological assemblage using an otolaryngological machine-learning model, identify an otolaryngological effect as a function of the otolaryngological localizer, wherein generating comprises receiving a normal operation as function of an otolaryngological recommendation, and identifying the otolaryngological effect as a function of the normal operation and otolaryngological localizer using an effect machine-learning model, ascertain an edible as a function of the otolaryngological effect, and generate a nourishment program as a function of the edible.

20 Claims, 7 Drawing Sheets

(56) References Cited

U.S. PATENT DOCUMENTS

2019/0371452 A1    12/2019  Mainardi
2020/0350053 A1*   11/2020  Cosse ................... G16H 30/40

OTHER PUBLICATIONS

Title: Optimization Approach On Nutritious Menu Planning For Sinusitis Patient Among Malaysian Date: Nov. 23, 2020 By: Sufahanu.
Title: Effect of Dietary Modification for Targeting Histamine Activity in Patients of Allergic Rhinitis: a Randomised Open Label Study Date: Apr. 2020 By: Khan.
Title: Maternal diet before and during pregnancy and risk of asthma and allergic rhinitis in children Date: Dec. 2019 By: Baiz.
Title: Food Intolerance Date: 1986 By: Loblay.
Title:Mediterranean diet is associated with reduced asthma and rhinitis in Mexican children Date: Sep. 8, 2008 By: De Battle.
Title: Dietary factors associated with wheezing and allergic rhinitis in children Date: Nov. 2, 20032 By: Farchi.

* cited by examiner

SYSTEM AND METHOD FOR GENERATING AN OTOLARYNGOLOGICAL DISEASE NOURISHMENT PROGRAM

FIELD OF THE INVENTION

The present invention generally relates to the field of artificial intelligence. In particular, the present invention is directed to a system and method for generating an otolaryngological disease nourishment program.

BACKGROUND

Current edible suggestion systems do not account for ocular measurements of an individual. This leads to inefficiency of an edible suggestion system and a poor nutrition plan for the individual. This is further complicated by a lack of uniformity of nutritional plans, which results in dissatisfaction of individuals.

SUMMARY OF THE DISCLOSURE

In an aspect a system for generating an otolaryngological disease nourishment program includes a computing device, the computing device configured to receive at least an otolaryngological component as a function of an otolaryngological system, determine an otolaryngological localizer as a function of the otolaryngological biomarker, wherein determining comprises obtaining at least an otolaryngological assemblage, and determining the otolaryngological localizer as a function of the otolaryngological biomarker and otolaryngological assemblage using an otolaryngological machine-learning model, identify an otolaryngological effect as a function of the otolaryngological localizer, wherein identifying comprises receiving a normal operation as function of an otolaryngological recommendation, and identifying the otolaryngological effect as a function of the normal operation and otolaryngological localizer using an effect machine-learning model, ascertain an edible as a function of the otolaryngological effect, and generate a nourishment program as a function of the edible.

In another aspect a method for generating an otolaryngological disease nourishment program includes receiving, by a computing device, at least an otolaryngological component as a function of an otolaryngological system, determining, by the computing device, an otolaryngological localizer as a function of the otolaryngological biomarker, wherein determining comprises obtaining at least an otolaryngological assemblage, and determining the otolaryngological localizer as a function of the otolaryngological biomarker and otolaryngological assemblage using an otolaryngological machine-learning model, identifying, by the computing device, an otolaryngological effect as a function of the otolaryngological localizer, wherein identifying comprises receiving a normal operation as function of an otolaryngological recommendation, and identifying the otolaryngological effect as a function of the normal operation and otolaryngological localizer using an effect machine-learning model, ascertaining, by the computing device, an edible as a function of the otolaryngological effect, and generating, by the computing device, a nourishment program as a function of the edible.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating an otolaryngological disease nourishment program. In an embodiment, this disclosure may receive at least an otolaryngological component as a function of an otolaryngological system. Aspects of the present disclosure can be used to determine an otolaryngological localizer as a function of the otolaryngological component. Aspects of the present disclosure can also be used to identify an otolaryngological effect as a function of the otolaryngological localizer. Aspects of the present disclosure can also be used to ascertain an edible as a function of the otolaryngological effect. This is so, at least in part, because this disclosure uses a machine-learning model. Aspects of the present disclosure allow for generating a nourishment program as a function of the edible. Exemplary embodiments illustrating aspects of the present disclosure are described below in the context of several specific examples.

Figure 1:
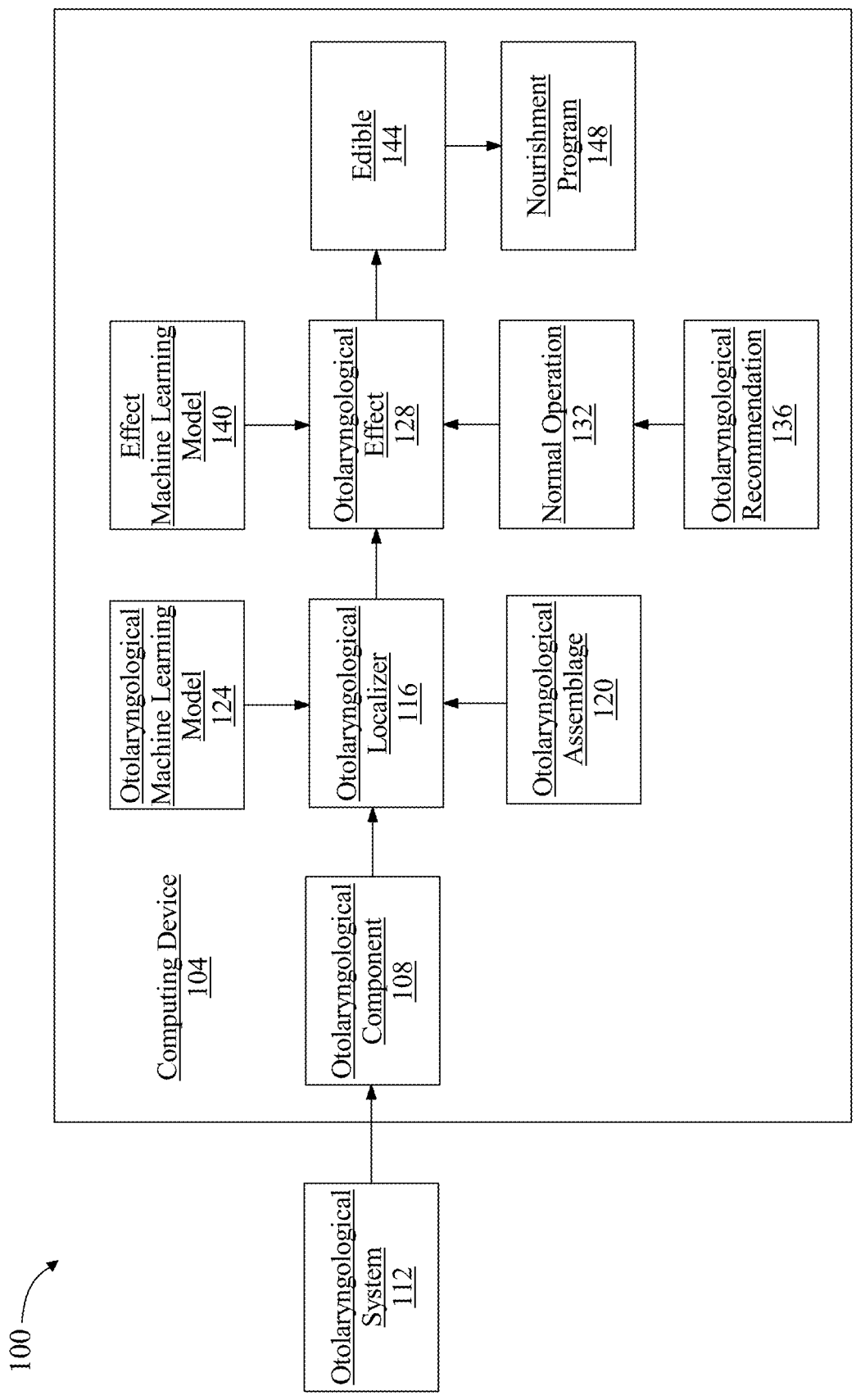
FIG. 1 is a block diagram illustrating an exemplary embodiment of a system for generating an otolaryngological disease nourishment program.

Referring now to FIG. 1, an exemplary embodiment of a system 100 for generating an otolaryngological disease nourishment program is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 receives at least an otolaryngological component 108 as a function of an otolaryngological system 112. As used in this disclosure "otolaryngological component" is an element of data that denotes an individual's otolaryngological system health status. Otolaryngological component 108 may include a biological sample. As used in this disclosure "biological sample" is one or more biological specimens collected from an individual. Biological sample may include, without limitation, exhalate, blood, sputum, urine, saliva, feces, semen, and other bodily fluids, as well as tissue. Otolaryngological component may include a biological sampling device. As used in this disclosure "biological sampling device" is one or more substances that are used to collect a biological sample, wherein a biological sample is described above. As a non-limiting example, biological sampling device may include oral swabs, nasal swabs, vestibular swabs, throat sample applicators, and the like thereof. Otolaryngological component 108 may include one or more biomarkers, wherein biomarkers are molecules and/or chemicals that at least identify the health status of a user's otolaryngological system. As a non-limiting example, biomarkers may include, Immunoglobulin Heavy constant gamma 1, regulator of G-protein signaling 10, chromosome 2 open reading frame 34, SH3-domain GRB2-like endophilin B1, Aminoacylase 1, cDNA, Calcium/calmodulin-dependent protein kinase IV, GSG1-like transcript variant, NIMA, UDP-Gal:betaGlcNAc beta 1,3-galactosyltransferase, polypeptide 4, Mitochondrial coil-coil domain protein 1, Neural Cell Adhesion Molecule 2, and the like thereof. As a further non-limiting example otolaryngological component 108 may include datum from one or more devices that collect, store, and/or calculate one or more lights, voltages, currents, sounds, chemicals, pressures, and the like thereof that are associated with the user's otolaryngological system. Otolaryngological component 108 is received as a function of an otolaryngological system 112. As used in this disclosure otolaryngological system 112 is an organ and/or tissue system that relates to an individual's ear, nose, throat, based of skull, head, and/or neck. As a non-limiting example otolaryngological system 112 may include organs and/or tissues such as the frontal sinus, ethmoid sinus, maxillary sinus, nostril, larynx, pharynx, adenoid, tonsil, vestibular canal, tympanic membrane, vocal cords, and the like thereof.

Still referring to FIG. 1, computing device 104 may obtain otolaryngological component 108 by receiving a diagnostic. As used in this disclosure "diagnostic" is an determination of an individual's otolaryngological system by an informed advisor. As a non-limiting example, diagnostic may include assessing an individual's larynx, hypopharynx, sinonasal cavity, nasopharyngeal system, thyroid, salivary gland, outer ear, middle ear, inner ear, facial nerve, balance, hearing, mucosal abundancy, nasal passages, environmental allergies, tonsils, vocal cords, trachea, and the like thereof. As a further non-limiting example, diagnostic may include the use of one or more diagnostic tools such as a Chiron lamp, Katz extractor, bull's eye lamp, speculum, Thudichum nasal speculum, St. Clair Thompson long bladed nasal speculum, Aural speculum, tongue depressor, forceps, eustachian catheter, laryngeal mirror, bronchoscope, oesophagoscope, post-nasal rhinoscopy mirror, tunning fork, otoscope, auriscope, aural snare, nasopharyngoscope, harpoon trocar, tracheal dilator, and the like thereof. As used in this disclosure "informed advisor" is an individual that is skilled in a particular area relating to the study of otolaryngology. As a non-limiting example an informed advisor may include a medical professional who may assist and/or participate in the medical treatment of an individual's otolaryngological system including, but not limited to, neurologists, family physicians, medical geneticists, immunologists, internists, and the like thereof. An informed advisor may include a/an otorhinolaryngologist, otologist, neurotologist, pediatric otorhinolaryngologist, laryngologist, plastic surgeon, general practitioner, family physician, and the like thereof.

Still referring to FIG. 1, computing device determines an otolaryngological localizer 116 as a function of the otolaryngological component 108. As used in this disclosure a "otolaryngological localizer" is a location within an otolaryngological system that is associated with otolaryngological component 108. As a non-limiting example, otolaryngological localizer 116 may identify the location of the vocal cords, larynx, and trachea as a function of otolaryngological components of reduced vocal capacity and shortness of breath. Additionally or alternatively, otolaryngological localizer 116 may identify a traverse parameter. As sued in this disclosure "traverse parameter" is one or more origination and termination locations of otolaryngological component 108. As a non-limiting example a bacterial infection associated with the pharynx may have traversed through the maxillary sinus to the ethmoid sinus, wherein traverse parameter may identify all three locations that otolaryngological component may traverse through. Traverse parameter may identify one or more progression states of otolaryngological component 108. As used in this disclosure "progression state" is the state of progress and/or advancement of otolaryngological component 108. Computing device 104 determines otolaryngological localizer 116 by obtaining at least an otolaryngological assemblage 120, wherein an "otolaryngological assemblage" is a group and/or assembly of tissues and/or organs in otolaryngological system 112, as described below, in reference to FIG. 2. As a non-limiting example, otolaryngological assemblage may include a/an laryngological assemblage, rhinological assemblage, neurtological assemblage, otological assemblage, and the like thereof.

Still referring to FIG. 1, computing device 104 determines otolaryngological localizer 116 as a function of otolaryngological component 108 and otolaryngological assemblage 120 using an otolaryngological machine-learning model 124. As used in this disclosure "otolaryngological machine-learning model" is a machine-learning model configured to produce an otolaryngological localizer output given otolaryngological component and otolaryngological assemblage as inputs; this is in contrast to a non-machine learning software program where the commands to be executed are determined in advance by a user and written in a programming language. Otolaryngological machine-learning model 124 may include one or more otolaryngological machine-learning processes such as supervised, unsupervised, or reinforcement machine-learning processes that computing device 104 and/or a remote device may or may not use in the determination of otolaryngological localizer 116. As used in this disclosure "remote device" is an external device to computing device 104. Otolaryngological machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train otolaryngological machine-learning process as a function of an otolaryngological training set. As used in this disclosure "otolaryngological training set" is a training set that correlates an otolaryngological component and/or otolaryngological assemblage to a otolaryngological localizer. For example, and without limitation, an otolaryngological assemblage associated with a rhinological assemblage and an otolaryngological component including mucosal production in the maxillary sinus may relate to a otolaryngological localizer of the nose and throat of the individual. Otolaryngological training set may be received as a function of user-entered valuations of otolaryngological assemblage, otolaryngological component, and/or otolaryngological localizer. Computing device 104 may receive otolaryngological training set by receiving correlations of otolaryngological assemblage and/or otolaryngological component that were previously received and/or determined during a previous iteration of determining otolaryngological localizer. The otolaryngological training set may be received by one or more remote devices that at least correlate an otolaryngological assemblage and otolaryngological component to an otolaryngological group, wherein a remote device is an external device to computing device 104, as described above. The otolaryngological training set may be received in the form of one or more user-entered correlations of an otolaryngological assemblage and otolaryngological component to an otolaryngological localizer. Additionally or alternatively, a user may include an informed advisor, wherein an informed advisor may include, without limitation, otorhinolaryngologists, otologists, neurotologists, pediatric otorhinolaryngologists, laryngologists, plastic surgeons, general practitioners, family physicians, and the like thereof.

Still referring to FIG. 1, computing device 104 may receive otolaryngological machine-learning model from the remote device that utilizes one or more otolaryngological machine learning processes, wherein a remote device is described above in detail. For example, and without limitation, a remote device may include a computing device, external device, processor, and the like thereof.

The remote device may perform the otolaryngological machine-learning process using the otolaryngological training set to determine otolaryngological localizer 116 and transmit the output to computing device 104. The remote device may transmit a signal, bit, datum, or parameter to computing device 104 that at least relates to ocular profile 116. Additionally or alternatively, the remote device may provide an updated machine-learning model. For example, and without limitation, an updated machine-learning model may be comprised of a firmware update, a software update, an otolaryngological machine-learning process correction, and the like thereof. As a non-limiting example a software update may incorporate a new otolaryngological assemblage that relates to a modified otolaryngological component. Additionally or alternatively, the updated machine learning model may be transmitted to the remote device, wherein the remote device may replace the machine machine-learning model with the updated machine-learning model and determine the otolaryngological localizer as a function of the otolaryngological assemblage using the updated machine-learning model. The updated machine-learning model may be transmitted by the remote device and received by computing device 104 as a software update, firmware update, or corrected otolaryngological machine-learning model. For example, and without limitation an otolaryngological machine-learning model may utilize a linear regression machine-learning process, wherein the updated machine-learning model may incorporate a gradient boosting machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 1, computing device 104 may determine otolaryngological localizer 116 by identifying an otolaryngological disease. As used in this disclosure "otolaryngological disease" is an ailment and/or collection of ailments that impact an individual's otolaryngological system. As a non-limiting example, otolaryngological disease may include Meniere's disease, patulous eustachian tube, chronic nosebleeds, sleep apnea, tinnitus, tonsilitis, allergies, vertigo, acid reflux, sinus infection, ear infection, Alport syndrome. Apert syndrome, Ayazi syndrome, bifid nose, cataract ataxia deafness, EEC syndrome, Fuhrmann syndrome, Kabuki syndrome, and the like thereof. Otolaryngological disease may be determined as a function of one or more disease machine-learning models. As used in this disclosure "disease machine-learning model" is a machine-learning model to produce an otolaryngological disease output given otolaryngological components as inputs; this is in contrast to a non-machine learning software program where the commands to be executed are determined in advance by a user and written in a programming language. Disease machine-learning model may include one or more disease machine-learning processes such as supervised, unsupervised, or reinforcement machine-learning processes that computing device 104 and/or a remote device may or may not use in the determination of otolaryngological disease. Disease machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train disease machine-learning process as a function of a disease training set. As used in this disclosure "disease training set" is a training set that correlates at least a disease enumeration and otolaryngological assemblage to an otolaryngological disease. As used in this disclosure "disease enumeration" is a measurable value associated with the otolaryngological component. As a non-limiting example a disease enumeration of 17 may be relate to an otolaryngological assemblage of a laryngological assemblage of the larynx, wherein an otolaryngological disease of larynx cancer may be identified. The disease training set may be received as a function of user-entered valuations of disease enumerations, otolaryngological assemblages, and/or otolaryngological diseases. Computing device 104 may receive disease training by receiving correlations of disease enumerations and/or otolaryngological assemblages that were previously received and/or determined during a previous iteration of determining otolaryngological diseases. The disease training set may be received by one or more remote devices that at least correlate a disease enumeration and/or otolaryngological assemblages effect to an otolaryngological disease, wherein a remote device is an external device to computing device 104, as described above. The disease training set may be received in the form of one or more user-entered correlations of a disease enumeration's and/or otolaryngological assemblage's effect with an otolaryngological disease. Additionally or alternatively, a user may include an informed advisor, wherein an informed advisor may include, without limitation, otorhinolaryngologists, otologists, neurotologists, pediatric otorhinolaryngologists, laryngologists, plastic surgeons, general practitioners, family physicians, and the like thereof.

Still referring to FIG. 1, computing device 104 may receive disease machine-learning model from the remote device that utilizes one or more disease machine learning processes, wherein a remote device is described above in detail. For example, and without limitation, a remote device may include a computing device, external device, processor, and the like thereof. The remote device may perform the disease machine-learning process using the disease training set to generate otolaryngological disease and transmit the output to computing device 104. The remote device may transmit a signal, bit, datum, or parameter to computing device 104 that at least relates to otolaryngological diseases. Additionally or alternatively, the remote device may provide an updated machine-learning model. For example, and without limitation, an updated machine-learning model may be comprised of a firmware update, a software update, a disease machine-learning process correction, and the like thereof. As a non-limiting example a software update may incorporate a new disease enumeration that relates to a modified otolaryngological assemblage. Additionally or alternatively, the updated machine learning model may be transmitted to the remote device, wherein the remote device may replace the disease machine-learning model with the updated machine-learning model and determine the otolaryngological disease as a function of the disease enumeration using the updated machine-learning model. The updated machine-learning model may be transmitted by the remote device and received by computing device 104 as a software update, firmware update, or corrected disease machine-learning model. For example, and without limitation disease machine-learning model may utilize a random forest machine-learning process, wherein the updated machine-learning model may incorporate linear regression machine-learning process.

Still referring to FIG. 1, computing device identifies an otolaryngological effect 128 as a function of otolaryngological localizer 116. As used in this disclosure "otolaryngological effect" is an impact and/or effect on the otolaryngological system of an individual. As a non-limiting example otolaryngological effect 128 may include runny nose, sore throat, coughing, sneezing, ear pain, hearing loss, snoring, obstructive sleep apnea, airway issues, difficulty breathing, mouth breathing, balance problems, sinus pressure, tonsil inflammation, tonsil infection, adenoid inflammation, adenoid infection, skin rash, ear noise, skin lesions, skin cancers, nose bleeds, thyroid mass, nasal congestion, nasal itching, nasal rubbing, dark circles under the eyes, hoarseness, frequent throat clearing, loss of smell, loss of taste, and the like thereof. Computing device identifies otolaryngological effect 128 by receiving a normal operation 132. As used in this disclosure "normal operation" is a reference operation and/or reference function for a normal physiologic component of a user's otolaryngological system, wherein a reference operation and/or reference function is a normal physiologic process that regularly occurs in the body. As a non-limiting example normal operation 132 may identify a normal function of the nose and throat glands to produce 1-2 quarts of mucus daily. As a further non-limiting example, normal operation 132 may identify a normal function of hearing that identifies an individual should be able to interpret sounds in the 20-20,000 Hz range. Normal operation 132 is received as a function of an otolaryngological recommendation 136. As used in this disclosure "otolaryngological recommendation" is a medical guideline that identifies the normal function and/or operation of the otolaryngological tissue health status. As a non-limiting example otolaryngological recommendation 136 may be identified by one or more organizations that relate to, represent, and/or study otolaryngological function in humans, such as American Academy of Otolaryngology, New England Otolaryngological Society, American Broncho-Esophagological Association, Massachusetts Society of Otolaryngology, and the like thereof. As a further non-limiting example, otolaryngological recommendation 136 may identify normal operation 132 as a function of one or more medical research journals, such as Journal of Otolaryngology Research, Otolaryngology Research and Reviews, Journal of the Association for Research in Otolaryngology, Research in Otolaryngology, The Lancet, New England Journal of Medicine, Science, Journal of the American Medical Association, and the like thereof.

Still referring to FIG. 1, computing device 104 identifies otolaryngological effect 128 as a function of normal operation 132 and otolaryngological localizer 116 using an effect machine-learning model 140. As used in this disclosure "effect machine-learning model" is a machine-learning model to produce an otolaryngological effect output given otolaryngological localizer and normal operation as inputs; this is in contrast to a non-machine learning software program where the commands to be executed are determined in advance by a user and written in a programming language. Effect machine-learning model 140 may include one or more effect machine-learning processes such as supervised, unsupervised, or reinforcement machine-learning processes that computing device 104 and/or a remote device may or may not use in the determination of otolaryngological effect. Effect machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train effect machine-learning process as a function of an effect training set. As used in this disclosure "effect training set" is a training set that correlates at least normal operation and otolaryngological localizer to otolaryngological effect. As a non-limiting example a normal operation of a sense of smell capability of 10,000 unique odors may be relate to an otolaryngological localizer of a nose and throat, wherein an otolaryngological effect of loss of sense of smell may be identified. The effect training set may be received as a function of user-entered valuations of normal operations, otolaryngological localizers, and/or otolaryngological effects. Computing device 104 may receive effect training by receiving correlations of normal operations and/or otolaryngological localizers that were previously received and/or determined during a previous iteration of determining otolaryngological effects. The effect training set may be received by one or more remote devices that at least correlate a normal operation and/or otolaryngological localizer effect to an otolaryngological effect, wherein a remote device is an external device to computing device 104, as described above. The effect training set may be received in the form of one or more user-entered correlations of a normal operation and otolaryngological localizer to an otolaryngological effect. Additionally or alternatively, a user may include an informed advisor, wherein an informed advisor may include, without limitation, otorhinolaryngologists, otologists, neurotologists, pediatric otorhinolaryngologists, laryngologists, plastic surgeons, general practitioners, family physicians, and the like thereof.

Still referring to FIG. 1, computing device 104 may receive effect machine-learning model 140 from the remote device that utilizes one or more effect machine learning processes, wherein a remote device is described above in detail. For example, and without limitation, a remote device may include a computing device, external device, processor, and the like thereof. The remote device may perform the effect machine-learning process using the effect training set to generate otolaryngological effect and transmit the output to computing device 104. The remote device may transmit a signal, bit, datum, or parameter to computing device 104 that at least relates to otolaryngological effects. Additionally or alternatively, the remote device may provide an updated machine-learning model. For example, and without limitation, an updated machine-learning model may be comprised of a firmware update, a software update, a effect machine-learning process correction, and the like thereof. As a non-limiting example a software update may incorporate a new normal operation that relates to a modified otolaryngological localizer. Additionally or alternatively, the updated machine learning model may be transmitted to the remote device, wherein the remote device may replace the effect machine-learning model with the updated machine-learning model and determine the otolaryngological effect as a function of the normal operation using the updated machine-learning model. The updated machine-learning model may be transmitted by the remote device and received by computing device 104 as a software update, firmware update, or corrected effect machine-learning model. For example, and without limitation effect machine-learning model may utilize a Naïve Bayes machine-learning process, wherein the updated machine-learning model may incorporate neural net machine-learning process.

Still referring to FIG. 1, computing device ascertains an edible 144 as a function of otolaryngological effect 128. As used in this disclosure an "edible" is a source of nourishment that may be consumed by a user such that the user may absorb the nutrients from the source. For example and without limitation, an edible may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. Computing device 104 may ascertain edible 144 as a function of obtaining a nourishment composition. As used in this disclosure "nourishment composition" is a list and/or compilation of all of the nutrients contained in an edible. As a non-limiting example nourishment composition may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition may be obtained as a function of an edible directory, wherein an edible directory is a database of edibles that may be identified as a function of one or more outline signatures, as described in detail below, in reference to FIG. 3.

Still referring to FIG. 1, computing device may ascertain edible 144 by identifying a relief parameter. As used in this disclosure "relief parameter" is a parameter that indicates the necessity for an edible to mitigate an irritation and/or allergic response. As a non-limiting example relief parameter may identify that an edible must mitigate an allergic response associated with anaphylaxis. As a further non-limiting example, relief parameter may identify that an edible may need to provide mild irritant reduction effects due to an irritant of capsaicin. Relief parameter may be identified by receiving at least an allergenic element of a user. As used in this disclosure "allergenic element" is a substance that causes an allergic reaction in the user's body. As a non-limiting example allergenic element may include pollen, animal dander, dust mites, mold, peanuts, tree nuts, wheat, soy nuts, shellfish, eggs, milk, bee venom, wasp venom, medications, antibiotics, latex, and the like thereof. Relief parameter may be obtaining at least an irritant component. As used in this disclosure "irritant component" is a substance that causes slight inflammation and/or discomfort in the body of the user. As a non-limiting example, irritant component may include one or more components such as chemicals, fragrances, metals, plants, medications, preservatives, antibiotics, acids, alkalis, body fluids, hair dyes, nail polish remover, paints, varnishes, soaps, detergents, resins, epoxies, and the like thereof.

Still referring to FIG. 1, computing device may ascertain edible by obtaining a severity index. As used in this disclosure "severity index" is a quantitative value of otolaryngological effect associated with the gravity and/or hardness of the effect. As a non-limiting example an otolaryngological effect of ringing in the ears may be a value of 7, wherein an otolaryngological effect of larynx blockage may have a value of 92. Computing device 104 may generate a degree of variance. As used in this disclosure "degree of variance" is a quantitative value comprising the magnitude of divergence of the severity index from a severity threshold. As used in this disclosure "severity threshold" is a quantitative value associated with the limit that an otolaryngological effect should have in the user body. For example, and without limitation, severity threshold may be 20 for the otolaryngological effect of deafness. As a non-limiting example, a degree of variance may be 7 for a severity index of 23 associated with mucus buildup in the sinus cavities, wherein the severity threshold is 16 for mucus buildup in the sinuses. Additionally or alternatively, severity threshold may include one or more thresholds associated with a quantitative property of an edible. As used in this disclosure "quantitative property" is the monetary value associated with an edible. As a non-limiting example a first threshold associated with a low degree of variance may identify an edible that has a low quantitative property. As a further non-limiting example a second threshold associated with a high degree of variance may identify an edible that has a high quantitative property. Degree of variance may include a transgression parameter. As used in this disclosure "transgression parameter" is a parameter that identifies one or more degrees of variance that exceed a variance limit. As a non-limiting example, transgression parameter may determine that a degree of variance should not exceed 12 for an hearing abnormality.

Still referring to FIG. 1, computing device 104 may ascertain edible 144 as a function of nourishment composition, otolaryngological effect 128, and an edible machine-learning model. As used in this disclosure "edible machine-learning model" is a machine-learning model to produce an edible output given nourishment compositions and outline signatures as inputs; this is in contrast to a non-machine learning software program where the commands to be executed are determined in advance by a user and written in a programming language. Edible machine-learning model may include one or more edible machine-learning processes such as supervised, unsupervised, or reinforcement machine-learning processes that computing device 104 and/or a remote device may or may not use in ascertaining edible 144. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process as a function of an edible training set. As used in this disclosure a "edible training set" is a training set that correlates at least nourishment composition and otolaryngological effect 128 to an edible. For example, and without limitation, nourishment composition of 4,700 mg of potassium and an otolaryngological effect of fluid buildup in the inner ear of an individual may relate to an edible of bananas. The edible training set may be received as a function of user-entered valuations of nourishment compositions, otolaryngological effects, and/or edibles. Computing device 104 may receive edible training by receiving correlations of nourishment compositions and/or otolaryngological effects that were previously received and/or determined during a previous iteration of determining edibles. The edible training set may be received by one or more remote devices that at least correlate a nourishment composition and otolaryngological effect to an edible, wherein a remote device is an external device to computing device 104, as described above. The edible training set may be received by one or more user-entered correlations of a nourishment composition and otolaryngological effect to an edible. Additionally or alternatively, a user may include an informed advisor, wherein an informed advisor may include, without limitation otorhinolaryngologists, otologists, neurotologists, pediatric otorhinolaryngologists, laryngologists, plastic surgeons, general practitioners, family physicians, and the like thereof.

Still referring to FIG. 1, edible machine-learning model may ascertain edible 144 as a function of one or more classifiers. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn as a function of a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may receive edible machine-learning model from the remote device that utilizes one or more edible machine learning processes, wherein a remote device is described above in detail. For example, and without limitation, a remote device may include a computing device, external device, processor, and the like thereof. The remote device may perform the edible machine-learning process using the edible training set to generate edible 144 and transmit the output to computing device 104. The remote device may transmit a signal, bit, datum, or parameter to computing device 104 that at least relates to edible 144. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified otolaryngological effect. Additionally or alternatively, the updated machine learning model may be transmitted to the remote device, wherein the remote device may replace the edible machine-learning model with the updated machine-learning model and determine the edible as a function of the otolaryngological effect using the updated machine-learning model. The updated machine-learning model may be transmitted by the remote device and received by computing device 104 as a software update, firmware update, or corrected edible machine-learning model. For example, and without limitation an edible machine-learning model may utilize a decision tree machine-learning process, wherein the updated machine-learning model may incorporate a logistic regression machine-learning process. Updated machine learning model may additionally or alternatively include any machine-learning model used as an updated machine learning model as described in U.S. Nonprovisional application Ser. No. 17/106,658.

Still referring to FIG. 1, computing device 104 may ascertain edible 144 as a function of a likelihood parameter. As used in this disclosure "likelihood parameter" is a parameter that identities the probability of a user to consume an edible. As a non-limiting example likelihood parameter may identify a high probability that a user will consume an edible of pasta. As a further non-limiting example likelihood parameter may identify a low probability that a user will consume an edible of broccoli. Likelihood parameter may be determined as a function of a user taste profile. As used in this disclosure "user taste profile" is a profile of a user that identifies one or more desires, preferences, wishes, and/or wants that a user has. As a non-limiting example a user taste profile may include a user's preference for cherry flavor and/or soft textured edibles. Likelihood parameter may be determined as a function of an edible profile. As used in this disclosure "edible profile" is taste of an edible is the sensation of flavor perceived in the mouth and throat on contact with the edible. Edible profile may include one or more flavor variables. As used in this disclosure "flavor variable" is a variable associated with the distinctive taste of an edible, wherein a distinctive may include, without limitation sweet, bitter, sour, salty, umami, cool, and/or hot. Edible profile may be determined as a function of receiving flavor variable as a function of a flavor directory. As used in this disclosure "flavor directory" is a database of flavors for an edible. As a non-limiting example flavor directory may include a list and/or collection of edibles that all contain sweet flavor variables. As a further non-limiting example flavor directory may include a list and/or collection of edibles that all contain salty flavor variables. Likelihood parameter may alternatively or additionally include any user taste profile and/or edible profile used as a likelihood parameter as described in U.S. Nonprovisional application Ser. No. 17/032,080, filed on Sep. 25, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

Still referring to FIG. 1, computing device 104 generates a nourishment program 148 as a function of edible 144. As used in this disclosure "nourishment program" is a program consisting of one or more edibles that are to be consumed over a given time period, wherein a time period is a temporal measurement such as seconds, minutes, hours, days, weeks, months, years, and the like thereof. As a non-limiting example nourishment program 148 may consist of recommending steak for 2 days. As a further non-limiting example nourishment program 148 may recommend tofu for a first day, ice cream for a second day, and bacon for a third day. Nourishment program 148 may include one or more diet programs such as paleo, keto, vegan, vegetarian, and the like thereof. Computing device 104 generates nourishment program as a function of a otolaryngological outcome. As used in this disclosure "otolaryngological outcome" is an outcome that an edible may generate according to a predicted and/or purposeful plan. As a non-limiting example, otolaryngological outcome may include a treatment outcome. As used in this disclosure "treatment outcome" is an intended outcome that is designed to at least reverse and/or eliminate otolaryngological effect 128 associated with otolaryngological localizer 116 and/or otolaryngological disease. As a non-limiting example, a treatment outcome may include reversing the effects of the otolaryngological disease of acrodysostosis. As a further non-limiting example, a treatment outcome includes reversing the otolaryngological disease of tinnitus. Otolaryngological outcome may include a prevention outcome.

As used in this disclosure "prevention outcome" is an intended outcome that is designed to at least prevent and/or avert otolaryngological effect 128 associated with otolaryngological localizer 116 and/or otolaryngological disease. As a non-limiting example, a prevention outcome may include preventing the development of the otolaryngological disease of sleep apnea.

Still referring to FIG. 1, computing device 104 may generate nourishment program 148 function of edible 144 and otolaryngological outcome using a nourishment machine-learning model. As used in this disclosure "nourishment machine-learning model" is a machine-learning model to produce a nourishment program output given edibles and/or otolaryngological outcomes as inputs; this is in contrast to a non-machine learning software program where the commands to be executed are determined in advance by a user and written in a programming language. Nourishment machine-learning model may include one or more nourishment machine-learning processes such as supervised, unsupervised, or reinforcement machine-learning processes that computing device 104 and/or a remote device may or may not use in the determination of nourishment program 148. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nourishment machine-learning process as a function of a nourishment training set. As used in this disclosure a "nourishment training set" is a training set that correlates a otolaryngological outcome to an edible. The nourishment training set may be received as a function of user-entered edibles, otolaryngological outcomes, and/or nourishment programs. Computing device 104 may receive nourishment training by receiving correlations of otolaryngological outcomes and/or edibles that were previously received and/or determined during a previous iteration of determining nourishment programs. The nourishment training set may be received by one or more remote devices that at least correlate a otolaryngological outcome and/or edible to a nourishment program, wherein a remote device is an external device to computing device 104, as described above. The nourishment training set may be received by one or more user-entered correlations of a otolaryngological outcome and edible to a nourishment program. Additionally or alternatively, a user may include an informed advisor, wherein an informed advisor may include, without limitation, otorhinolaryngologists, otologists, neurotologists, pediatric otorhinolaryngologists, laryngologists, plastic surgeons, general practitioners, family physicians, and the like thereof.

Still referring to FIG. 1, computing device 104 may receive nourishment machine-learning model 144 from the remote device that utilizes one or more nourishment machine learning processes, wherein a remote device is described above in detail. For example, and without limitation, a remote device may include a computing device, external device, processor, and the like thereof. The remote device may perform the nourishment machine-learning process using the nourishment training set to generate nourishment program 148 and transmit the output to computing device 104. The remote device may transmit a signal, bit, datum, or parameter to computing device 104 that at least relates to nourishment program 148. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new otolaryngological outcome that relates to a modified edible. Additionally or alternatively, the updated machine learning model may be transmitted to the remote device, wherein the remote device may replace the nourishment machine-learning model with the updated machine-learning model and determine the nourishment program as a function of the otolaryngological outcome using the updated machine-learning model. The updated machine-learning model may be transmitted by the remote device and received by computing device 104 as a software update, firmware update, or corrected nourishment machine-learning model. For example, and without limitation nourishment machine-learning model may utilize a heuristic algorithm machine-learning process, wherein the updated machine-learning model may incorporate nearest neighbor machine-learning processes.

Figure 2:
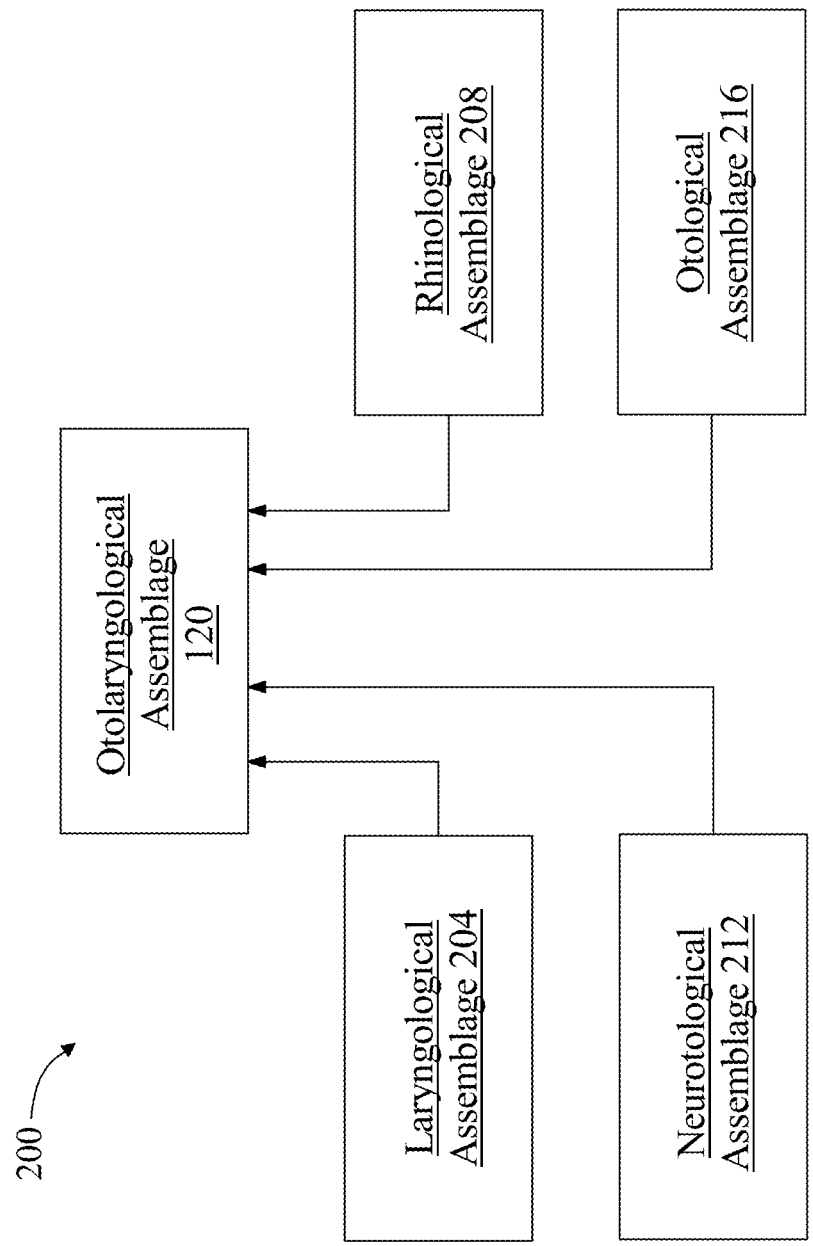
FIG. 2 is a block diagram of an exemplary embodiment of an otolaryngological assemblage according to an embodiment of the invention.

Now referring to FIG. 2, an exemplary embodiment 200 of an otolaryngological assemblage 120 according to an embodiment of the invention is illustrated. Otolaryngological assemblage 120 may include a laryngological assemblage 204. As used in this disclosure "laryngological assemblage" is an assemblage relating to one or more diseases and/or injuries associated with the larynx. As a non-limiting example, laryngological assemblage 204 may include, dysphonia component, a spasmodic dysphonic component, tracheostomic component, a vocologic component, and the like thereof. Otolaryngological assemblage 120 may include a rhinological assemblage 208. As used in this disclosure "rhinological assemblage" is an assemblage relating to one or more diseases and/or injuries associated with the nasal cavity and sinuses components. As a non-limiting example, rhinological assemblage 208 may include a nasal obstruction component, nasal septum deviation component, sinusitis component, allergy component, rhinitis component, pituitary component, empty nose syndrome component, and the like thereof. Otolaryngological assemblage 120 may include a neurotological assemblage 212. As used in this disclosure "neurotological assemblage" is an assemblage relating to one or more diseases and/or injuries associated with the neural function of the otolaryngological system. As a non-limiting example, neurotological assemblage 212 may include a vestibular neuronitis component, acoustic neuroma component, facial nerve paralysis component, neural hearing loss component, and the like thereof. Otolaryngological assemblage 120 may include a otological assemblage 216. As used in this disclosure "otological assemblage" is an assemblage relating to one or more diseases and/or injuries associated with the anatomy and/or physiologic of the ear. As a non-limiting example, otological assemblage 216 may include a/an outer ear disease component, middle ear disease component, inner ear disease component, and the like thereof.

Figure 3:
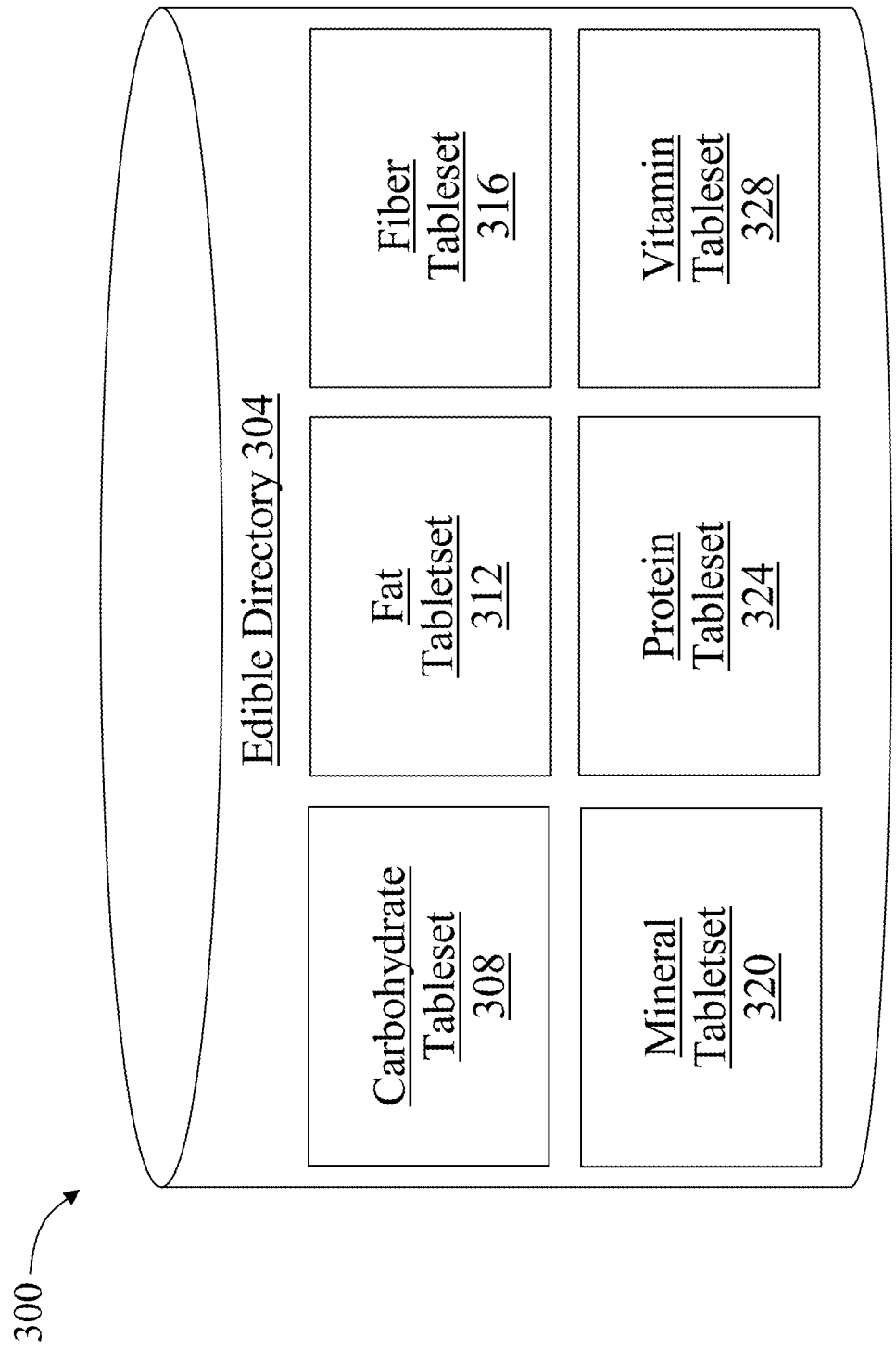
FIG. 3 is a block diagram of an exemplary embodiment of an edible directory according to an embodiment of the invention.

Now referring to FIG. 3, an exemplary embodiment 300 of an edible directory 304 according to an embodiment of the invention is illustrated. Edible directory 304 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 304 may alternatively or additionally be implemented using a distributed data storage protocol and/or data structure, such as a distributed hash table or the like. Edible directory 304 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 304 may include a carbohydrate tableset 308. Carbohydrate tableset 308 may relate to a nourishment composition of an edible with respect to the quantity and/or type of carbohydrates in the edible. As a non-limiting example, carbohydrate tableset 308 may include monosaccharides, disaccharides, oligosaccharides, polysaccharides, and the like thereof. Edible directory 304 may include a fat tableset 312. Fat tableset 312 may relate to a nourishment composition of an edible with respect to the quantity and/or type of esterified fatty acids in the edible. Fat tableset 312 may include, without limitation, triglycerides, monoglycerides, diglycerides, phospholipids, sterols, waxes, and free fatty acids. Edible directory 304 may include a fiber tableset 316. Fiber tableset 316 may relate to a nourishment composition of an edible with respect to the quantity and/or type of fiber in the edible. As a non-limiting example, fiber tableset 316 may include soluble fiber, such as beta-glucans, raw guar gum, psyllium, inulin, and the like thereof as well as insoluble fiber, such as wheat bran, cellulose, lignin, and the like thereof. Edible directory 304 may include a mineral tableset 320. Mineral tableset 320 may relate to a nourishment composition of an edible with respect to the quantity and/or type of minerals in the edible. As a non-limiting example, mineral tableset 320 may include calcium, phosphorous, magnesium, sodium, potassium, chloride, sulfur, iron, manganese, copper, iodine, zing, cobalt, fluoride, selenium, and the like thereof. Edible directory 304 may include a protein tableset 324. Protein tableset 324 may relate to a nourishment composition of an edible with respect to the quantity and/or type of proteins in the edible. As a non-limiting example, protein tableset 324 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory 304 may include a vitamin tableset 328. Vitamin tableset 328 may relate to a nourishment composition of an edible with respect to the quantity and/or type of vitamins in the edible. As a non-limiting example, vitamin tableset 328 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 4:
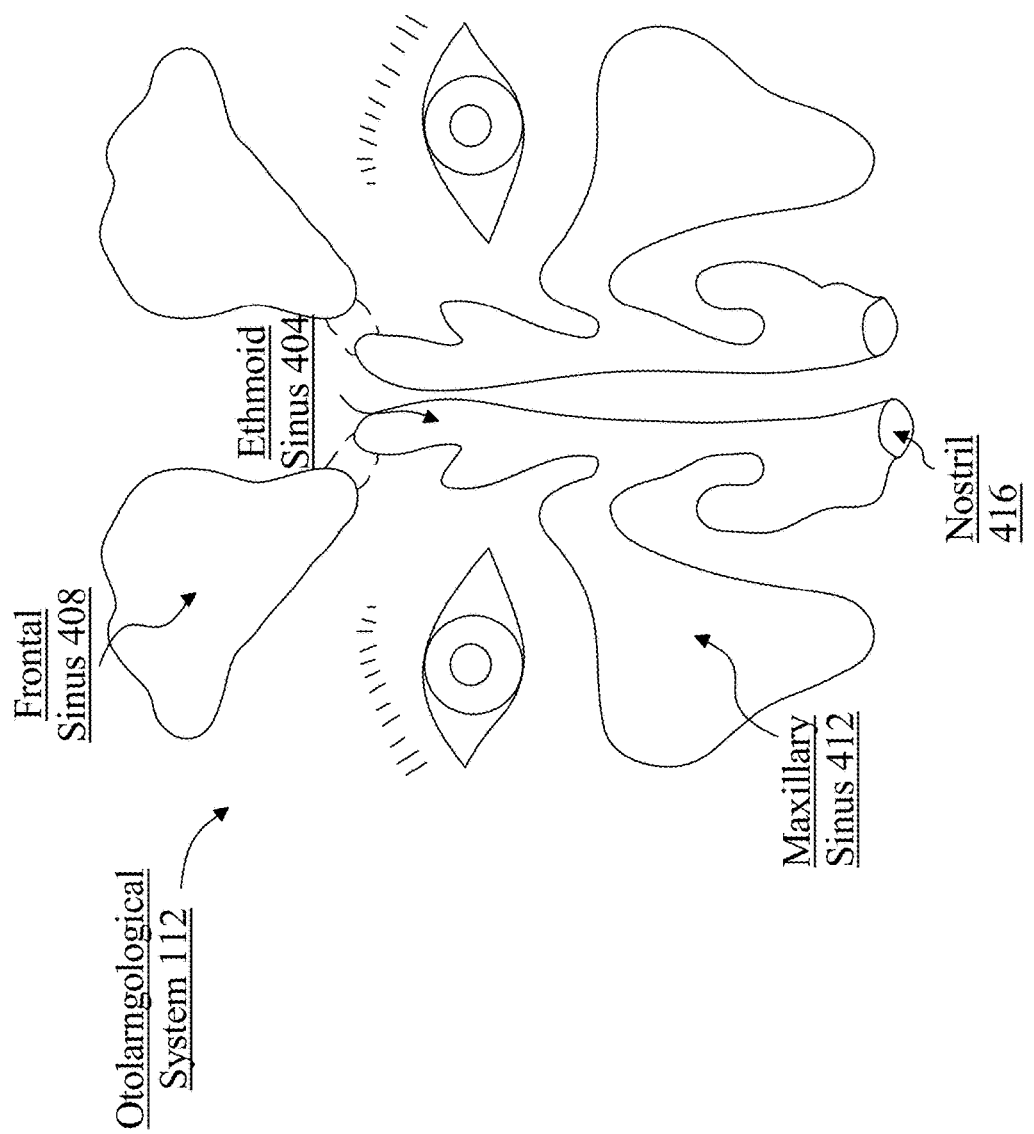
FIG. 4 is a block diagram of an exemplary embodiment of an otolaryngological system according to an embodiment of the invention.

Now referring to FIG. 4, an exemplary embodiment of otolaryngological system 112 according to an embodiment of the invention is illustrated. Otolaryngological system 112 may include an ethmoid sinus 404. As sued in this disclosure "ethmoid sinus" is one or more cavities of a user sinus system that is located on each side of the bridge of the nose, near the eyes. As a non-limiting example, ethmoid sinus 404 may be located in the ethmoid bone, which separates the nasal cavity from the brain. As a further non-limiting example ethmoid sinus 404 may include 6-12 small air cells that open independently into the nasal cavity of an individual. Otolaryngological system 112 may include a frontal sinus 408. As used in this disclosure "frontal sinus" is one or more cavities located above the nears, near an individual's forehead. As a non-limiting example, frontal sinus 408 may include sinus cavities that are located in the center of the frontal bone just above each eye. Otolaryngological system 112 may include a maxillary sinus 412. As used in this disclosure "maxillary sinus" is one or more cavities located on each side of the nose, near the cheek bones. As a non-limiting example, maxillary sinus 412 may include sinus cavities that behind the cheekbones near the maxillae and/or upper jaws. Otolaryngological system 112 may include a maxillary sinus. As used in this disclosure "nostril" is one or more openings of the nose that at least allow ambient gases to enter the nasal cavity. As a non-limiting example, nostril 416 may include two channels that bifurcate to an external opening that is used for the passage of gasses.

Figure 5:
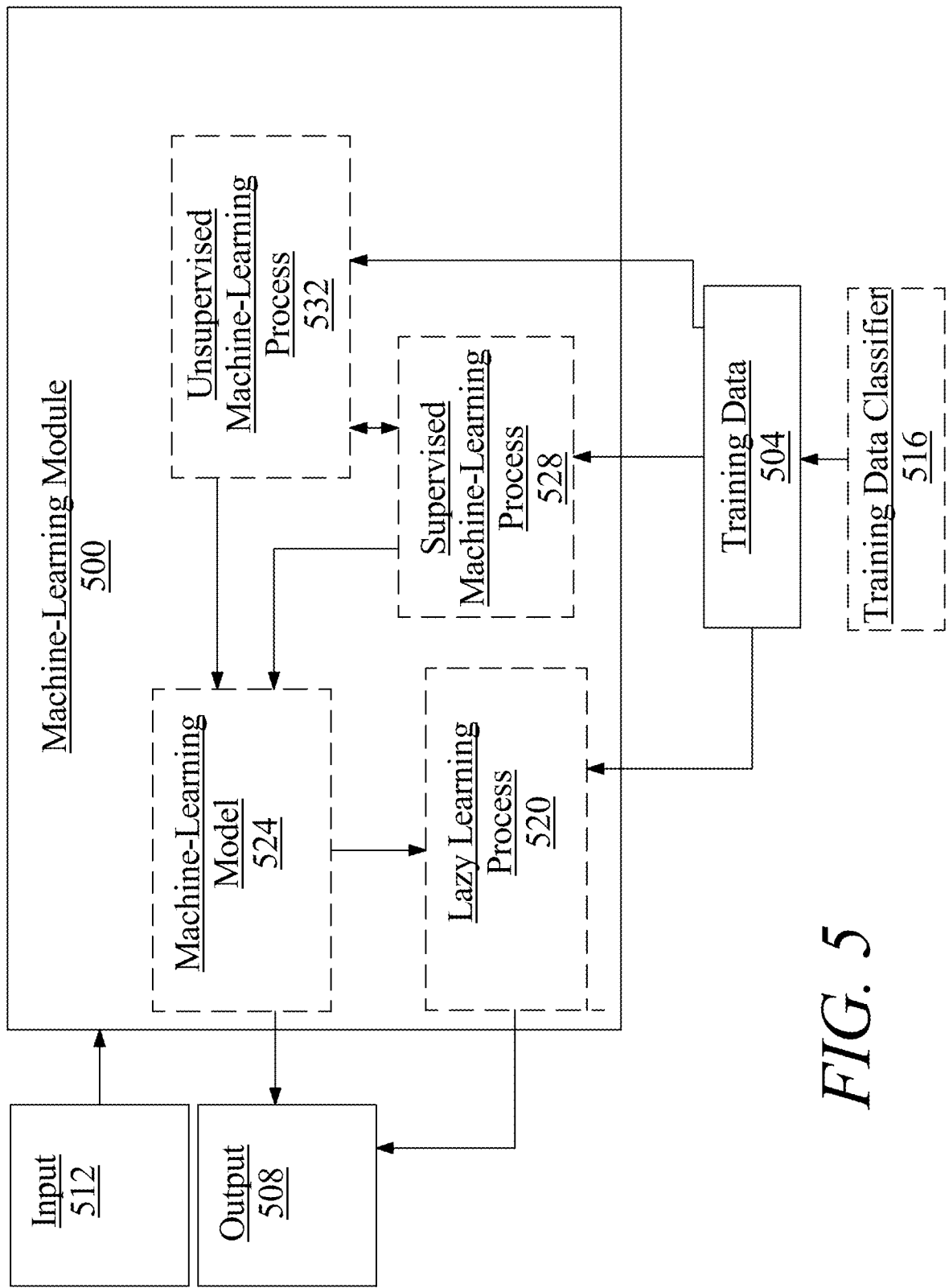
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs may include an otolaryngological component and/or otolaryngological assemblage, wherein an output may include an otolaryngological localizer.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to sub-categories of otolaryngological assemblages such as a facial assemblage, laryngological assemblage, pediatric assemblage, rhinological assemblage, neurotological assemblage, otological assemble, cranial assemblage, transfer assemblage, and the like thereof.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include otolaryngological components and/or otolaryngological assemblages as described above as inputs, otolaryngological localizers as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms.

Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
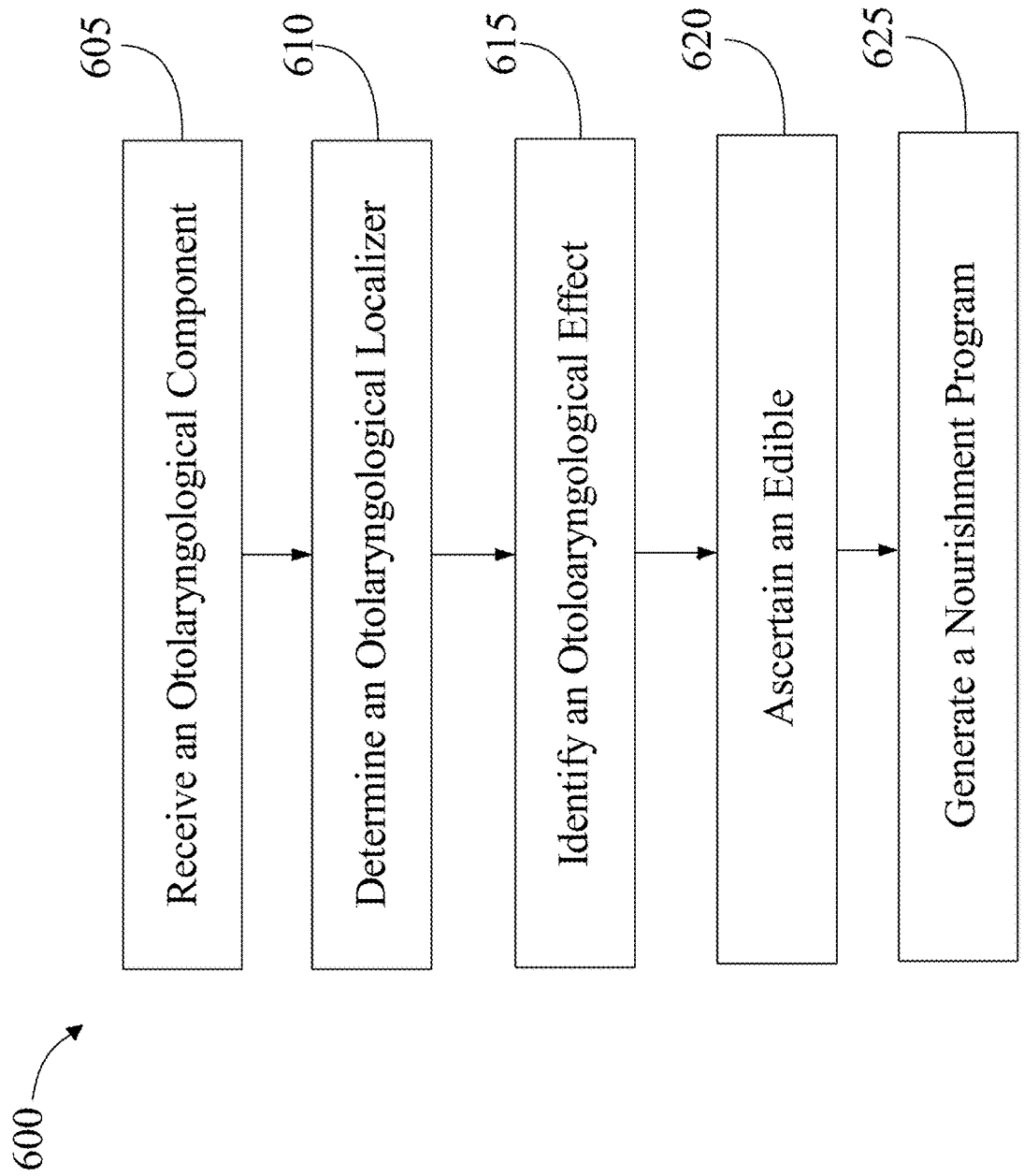
FIG. 6 is a process flow diagram illustrating an exemplary embodiment of a method of generating an otolaryngological disease nourishment program.

Now referring to FIG. 6, an exemplary embodiment of a method 600 for generating an otolaryngological disease nourishment program is illustrated. At step 605, a computing device 104 receives at least an otolaryngological component 108 as a function of an otolaryngological system 112. Computing device 104 includes any of the computing device as described above, in reference to FIGS. 1-5. Otolaryngological component 108 includes any of the otolaryngological component 108 as described above, in reference to FIGS. 1-5. Otolaryngological system 112 includes any of the otolaryngological system 112 as described above, in reference to FIGS. 1-5.

Still referring to FIG. 6, at step 610, computing device 104 determines an otolaryngological localizer 116 as a function of otolaryngological component 108. Otolaryngological localizer 116 includes any of the otolaryngological localizer 116 as described above, in reference to FIGS. 1-5. Computing device 104 determines otolaryngological localizer 116 by obtaining at least an otolaryngological assemblage 120. Otolaryngological assemblage 120 includes any of the otolaryngological assemblage 120 as described above, in reference to FIGS. 1-5. Computing device 104 determines the otolaryngological localizer 116 as a function of the otolaryngological component 108 and otolaryngological assemblage 120 using an otolaryngological machine-learning model 124. Otolaryngological machine-learning model 124 includes any of the otolaryngological machine-learning model 124 as described above, in reference to FIGS. 1-5.

Still referring to FIG. 6, at step 615, computing device 104 identifies an otolaryngological effect 128 as a function of the otolaryngological localizer 116. Otolaryngological effect 128 includes any of the otolaryngological effect 128 as described above, in reference to FIGS. 1-5. Computing device 104 identifies otolaryngological effect 128 by receiving a normal operation 132 as a function of an otolaryngological recommendation 136. Normal operation 132 includes any of the normal operation 132 as described above, in reference to FIGS. 1-5. Otolaryngological recommendation 136 includes any of the otolaryngological recommendation 136 as described above, in reference to FIGS. 1-5. Computing device 104 identifies otolaryngological effect 128 as a function of normal operation 132 and otolaryngological localizer 116 using an effect machine-learning model 140. Effect machine-learning model 140 includes any of the effect machine-learning model 140 as described above, in reference to FIGS. 1-5.

Still referring to FIG. 6, at step 620, computing device 104 ascertains at least an edible 144 as a function of otolaryngological effect 128. Edible 144 includes any of the edible 144 as described above, in reference to FIGS. 1-5.

Still referring to FIG. 6, at step 625, computing device 104, generates a nourishment program 148 as a function of edible 144. Nourishment program 148 includes any of the nourishment program 148 as described above, in reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
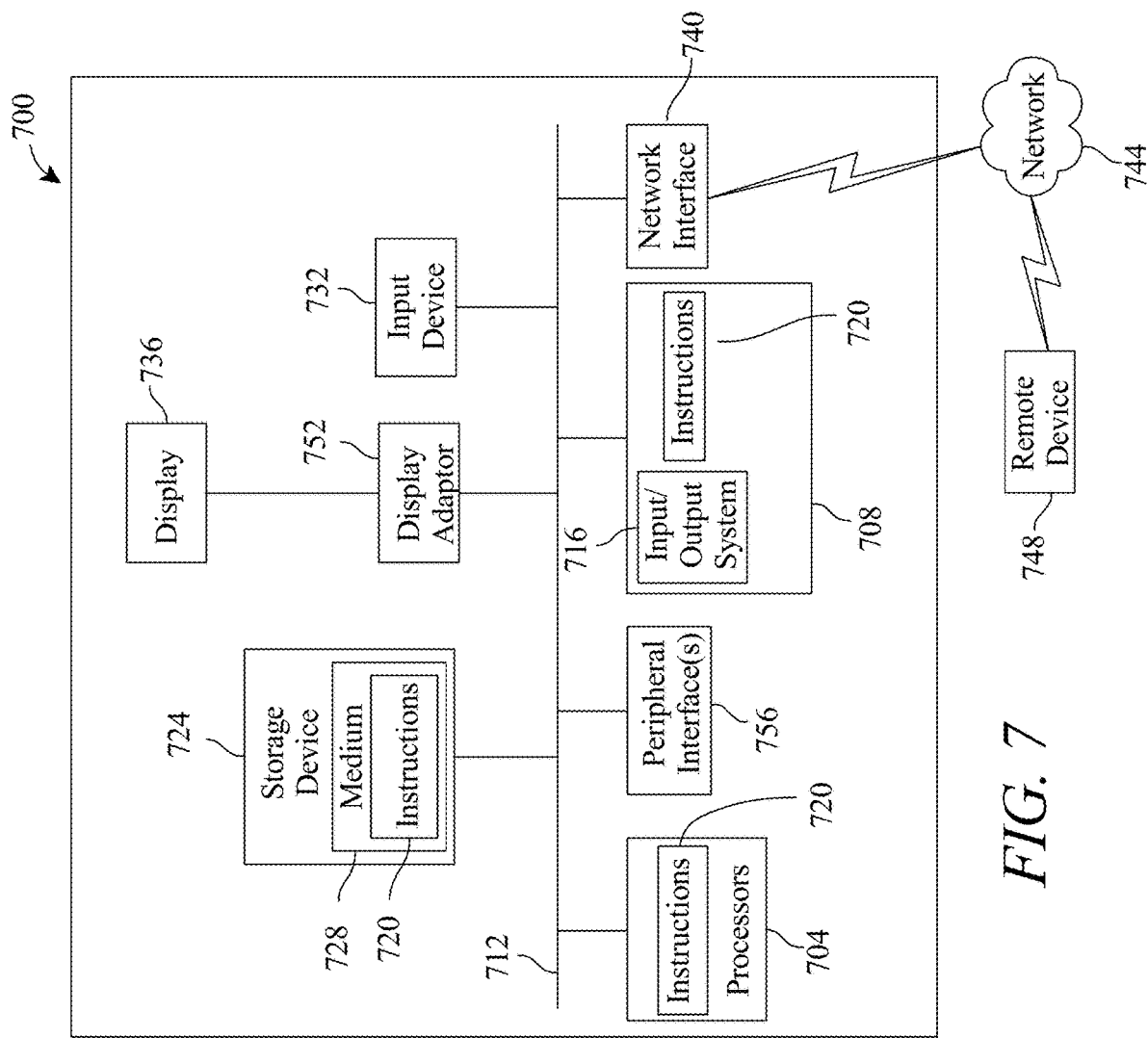
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIRE-WIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating an otolaryngological disease nourishment program, the system comprising:
   a computing device, the computing device configured to:
   receive at least an otolaryngological component as a function of an otolaryngological system;
   determine an otolaryngological localizer as a function of the at least an otolaryngological component, wherein determining comprises:
     obtaining at least an otolaryngological assemblage; and
     determining the otolaryngological localizer as a function of the at least an otolaryngological component and otolaryngological assemblage using an otolaryngological machine-learning model, wherein the otolaryngological machine-learning model is trained as a function of an otolaryngological training set that correlates the otolaryngological component and the otolaryngological assemblage to the otolaryngological localizer;
   identify an otolaryngological effect as a function of the otolaryngological localizer, wherein identifying comprises:
     receiving a normal operation as a function of an otolaryngological recommendation; and
     identifying the otolaryngological effect as a function of the normal operation and otolaryngological localizer using an effect machine-learning model;
   ascertain an edible as a function of the otolaryngological effect; and
   generate a nourishment program as a function of the edible.

2. The system of claim 1, wherein receiving the at least an otolaryngological component includes obtaining a diagnostic and receiving the at least an otolaryngological component as a function of the diagnostic.

3. The system of claim 1, wherein determining the otolaryngological localizer includes identifying an otolaryngological disease and determining the otolaryngological localizer as a function of the otolaryngological disease.

4. The system of claim 3, wherein identifying the otolaryngological disease further comprises:
   obtaining a disease training set; and
   determining the otolaryngological disease as a function of the at least an otolaryngological component, otolaryngological assemblage, and disease training set using disease machine-learning model, wherein the disease machine-learning model is trained as a function of the disease training set.

5. The system of claim 1, wherein ascertaining the edible further comprises identifying a relief parameter and ascertaining the edible as a function of the relief parameter.

6. The system of claim 5, wherein identifying the relief parameter further comprises:
   receiving at least an allergenic element of a user;
   obtaining at least an irritant component; and
   determining the relief parameter as a function of the allergenic element and the at least an irritant component.

7. The system of claim 1, wherein ascertaining the edible further comprises:
   obtaining a severity index;
   generating a degree of variance; and
   ascertaining the edible as a function of the degree of variance and the severity index.

8. The system of claim 1, wherein ascertaining the edible further comprises:
   obtaining a nourishment composition from an edible directory; and
   ascertaining the edible using the nourishment composition, the otolaryngological effect, and an edible machine-learning model.

9. The system of claim 1, wherein ascertaining the edible further comprises:
   generating a likelihood parameter, wherein the likelihood parameter relates a user taste profile to an edible profile; and
   ascertaining the edible as a function of the likelihood parameter.

10. The system of claim 1, wherein generating the nourishment program further comprises:
    obtaining an otolaryngological outcome; and
    generating the nourishment program as a function of the edible and otolaryngological outcome using a nourishment machine-learning model.

11. A method for generating an otolaryngological disease nourishment program, the method comprising:
    receiving, by a computing device, at least an otolaryngological component as a function of an otolaryngological system;
    determining, by the computing device, an otolaryngological localizer as a function of the at least an otolaryngological component, wherein determining comprises:
       obtaining at least an otolaryngological assemblage; and
       determining the otolaryngological localizer as a function of the at least an otolaryngological component and otolaryngological assemblage using an otolaryngological machine-learning model, wherein the otolaryngological machine-learning model is trained as a function of an otolaryngological training set that corelates the otolaryngological component and the otolaryngological assemblage to the otolaryngological localizer;
    identifying, by the computing device, an otolaryngological effect as a function of the otolaryngological localizer, wherein identifying comprises:
       receiving a normal operation as a function of an otolaryngological recommendation; and
       identifying the otolaryngological effect as a function of the normal operation and otolaryngological localizer using an effect machine-learning model;
    ascertaining, by the computing device, an edible as a function of the otolaryngological effect; and
    generating, by the computing device, a nourishment program as a function of the edible.

12. The method of claim 11, wherein receiving the at least an otolaryngological component includes obtaining a diagnostic and receiving the at least an otolaryngological component as a function of the diagnostic.

13. The method of claim 11, wherein determining the otolaryngological localizer includes identifying an otolaryngological disease and determining the otolaryngological localizer as a function of the otolaryngological disease.

14. The method of claim 13, wherein identifying the otolaryngological disease further comprises:
    obtaining a disease training set; and
    determining the otolaryngological disease as a function of the at least an otolaryngological component, otolaryngological assemblage, and disease training set using disease machine-learning model, wherein the disease machine-learning model is trained as a function of the disease training set.

15. The method of claim 11, wherein ascertaining the edible further comprises identifying a relief parameter and ascertaining the edible as a function of the relief parameter.

16. The method of claim 15, wherein identifying the relief parameter further comprises:
    receiving at least an allergenic element of a user;
    obtaining at least an irritant component; and
    determining the relief parameter as a function of the allergenic element and the at least an irritant component.

17. The method of claim 11, wherein ascertaining the edible further comprises:
    obtaining a severity index;
    generating a degree of variance; and
    ascertaining the edible as a function of the degree of variance and the severity index.

18. The method of claim 11, wherein ascertaining the edible further comprises:
    obtaining a nourishment composition from an edible directory; and
    ascertaining the edible using the nourishment composition, the otolaryngological effect, and an edible machine-learning model.

19. The method of claim 11, wherein ascertaining the edible further comprises:
    generating a likelihood parameter, wherein the likelihood parameter relates a user taste profile to an edible profile; and
    ascertaining the edible as a function of the likelihood parameter.

20. The method of claim 11, wherein generating the nourishment program further comprises:
    obtaining an otolaryngological outcome; and
    generating the nourishment program as a function of the edible and otolaryngological outcome using a nourishment machine-learning model.

* * * * *